United States Patent [19]

Wang et al.

[11] 3,939,115

[45] Feb. 17, 1976

[54] POLYCHROMOPHORIC ULTRAVIOLET STABILIZERS AND THEIR USE IN ORGANIC COMPOSITIONS

[75] Inventors: Richard H. S. Wang; Gether Irick, Jr., both of Kingsport, Tenn.

[73] Assignee: Eastman Kodak Company, Rochester, N.Y.

[22] Filed: Oct. 2, 1974

[21] Appl. No.: 511,331

[52] U.S. Cl. 260/45.8 N; 260/45.8 NZ; 260/45.8 SN
[51] Int. Cl.² ................... C08K 5/00; C08L 5/00
[58] Field of Search 260/45.8 N, 45.8 NZ, 45.8 SN; 106/176

[56] References Cited
UNITED STATES PATENTS

| | | | |
|---|---|---|---|
| 3,551,443 | 12/1970 | Duennenberger | 260/45.8 NZ |
| 3,660,125 | 5/1972 | Buell | 260/45.8 NZ |

*Primary Examiner*—Donald E. Czaja
*Assistant Examiner*—William E. Parker

[57] ABSTRACT

The invention relates to polychromophoric compounds which have been found to be effective ultraviolet stabilizers. The invention also relates to ultraviolet degradable organic compositions containing a stabilizing amount of the polychromophoric composition to prevent such degradation. These stabilizers are effective in the presence of other additives commonly employed in polymeric compositions including, for example, pigments, colorants, fillers, reinforcing agents and the like. These ultraviolet stabilizers may also be incorporated into the organic compositions in the polymer melt or dissolved in the polymer dope, coated on the exterior of the molded article, film or extruded fiber.

30 Claims, No Drawings

POLYCHROMOPHORIC ULTRAVIOLET STABILIZERS AND THEIR USE IN ORGANIC COMPOSITIONS

This invention relates to polychromophoric ultraviolet stabilizers and their use in organic compositions. More particularly, the invention relates to polychromophoric compositions and the stabilization of ultraviolet degradable organic compositions against deterioration resulting from the exposure to such radiations with such polychromophoric compositions.

The degradative effects of ultraviolet light on various organic compositions is well known in the art. The photo-deterioration or degradation is of particular concern with organic photo-degradable compositions which are exposed to ultraviolet light, such as sunlight, for long periods of time. One group of such photo-degradable organic compositions are polymeric compositions such as polyolefins, polyesters and the like. On exposure to sunlight for extended periods of time, these polymeric compositions degrade and their physical properties are reduced to render the polymeric composition less useful for most applications. Therefore, considerable effort has been directed to providing a solution to the photo-degradation problem of polymeric compositions. As a result of this effort, there have been discovered many additives and stabilizers which improve the stability of polymeric compositions.

Moreover, various additives and stabilizers exhibit the power to absorb ultraviolet radiation within the band of 2900 to 4000 A. and, when incorporated in various plastic materials such as transparent sheets, the resultant sheet acts as a filter for all the radiation passing through and will transmit only such radiations as are not absorbed by the sheet and/or the absorbing agent. It is thus possible to screen out undesirable radiations and utilize the resulting transparent sheet as a filter in many technical and commercial applications, such as wrappings for food products and the like.

While there are many additives, stabilizers and mixtures thereof which are known in the art to improve the ultraviolet light stability of organic compositions, there is a need in the art for more efficient and effective stabilizers to prevent the photo-degradation of organic compositions susceptible to photo-degradation. Therefore, to provide a more effective and efficient ultraviolet stabilizer for organic compositions susceptible to such degradation would be an advance in the state of the art.

It is, therefore, an object of the present invention to provide more effective and efficient ultraviolet light stabilizer compositions.

Another object of the present invention is to provide useful compositions characterized by improved resistance to ultraviolet degradation and deterioration.

A further object of the present invention is to provide compositions containing polychromophoric compositions which are resistant to ultraviolet degradation.

Another and further obejct of this invention is to provide processes for improving the resistance of organic materials to deterioration and degradation by actinic radiation and especially ultraviolet radiation.

A still further object of this invention is to provide compositions and processes for improving the resistance of organic materials to deterioration and degradation by actinic radiations, including short wavelength visible radiations.

Further objects and advantages of the invention will be apparent to those skilled in the art from the accompanying disclosure and claims.

In accordance with the present invention, polychromophoric compositions are provided which are useful as ultraviolet stabilizers or ultraviolet screening agents. These organic compositions contain at least one heterocyclic group containing compositions connected to an aromatic moiety. The polychromophoric compositions of the present invention have the following structure:

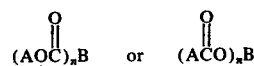

wherein A is a group having the structure

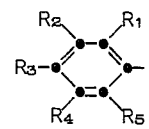

$R_1$, $R_2$, $R_3$, $R_4$ and $R_5$ are hydrogen, hydroxy, lower alkyl or substituted lower alkyl groups having 1 to 12 carbon atoms, cycloalkyl or substituted cycloalkyl, aryl or substituted aryl having 6 to 18 carbon atoms, lower alkylaryl, chloro, bromo, fluoro, alkoxy, aryloxy, substituted amino, cyano, carboalkoxy and the substituents $R_1$ and $R_2$, $R_2$ and $R_3$, $R_3$ and $R_4$, and $R_4$ and $R_5$, combined with the carbon atoms to which they are attached, are joined alkylene groups completing a carbocyclic ring, which ring can also be substituted with one or more of the substituents listed above for $R_1$, $R_2$, $R_3$, $R_4$ and $R_5$. It is necessary that at least one of $R_1$ or $R_5$ be hydrogen, so that on exposure to ultraviolet light, the heterocyclic bisphenyl ester is capable by the "Photo-Fries" rearrangement of forming a phenol group in that position formerly joined through an oxygen atom to the carbonyl linking group.

B is a heterocyclic phenyl group having the structure

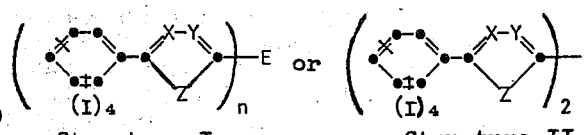

Structure I                Structure II wherein X and Y are a carbon atom or a nitrogen atom; Z is an oxygen atom, a sulfur atom, or a nitrogen atom containing a hydrogen atom or a substituted or unsubstituted lower alkyl group having 1 to 12 carbon atoms; I is hydrogen, fluoro, chloro, bromo, lower alkyl, substituted lower alkyl, cycloalkyl, substituted cycloalkyl, aryl substituted aryl, lower alkylaryl, alkoxy, aryloxy, substituted amino, and cyano. I is present on all positions of the benzenoid ring, except the carbon atom attached to the heterocyclic ring and the carbon atom attached to the carbonyloxy or oxycarbonyl group. When the heterocyclic bisphenyl ester is structure II, it is necessary that at least one of I, ortho to the carbon atom attached to oxycarbonyl group be hydrogen, so that on exposure to ultraviolet light, the heterocyclic bisphenyl ester is capable by the "Photo-Fries" rearrangement of forming a phenol group in that position formerly joined through an oxygen atom to the carbonyl linkage group.

E is substituted or unsubstituted alkylene and arylene; n is an integer from 1 to 6.

Suitable A groups are phenyl, naphthyl, 2,4-di-t-butylphenyl, 2-t-butyl-4-methylphenyl, 3-methoxyphenyl, 3-chlorophenyl, 4-acetamidophenyl, 4-carbomethoxyphenyl and the like.

Suitable B groups are, for example, moieties having the structure:

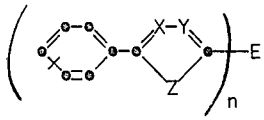

and

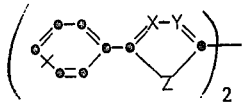

and include substituted and unsubstituted 1,3,4-oxadiazol-2,5-diyl, 1,3,4-thiadiazol-2,5-diyl, 1,2,4-triazol-3,5-diyl, oxazol-diyl, thiazoldiyl and imidazoldiyl and the like.

Examples of suitable 1,3,4-oxadiazol-2,5-diyl moieties are those having the structures:

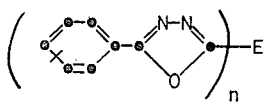

and

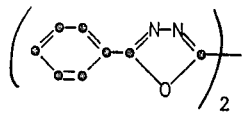

wherein E is a substituted or unsubstituted alkylene having 1 to 12 carbon atoms or arylene having 6 to 18 carbon atoms; n is an integer from 1 to 6; such as 4,4'-(1,3,4-oxadiazol-2,5-diyl)diphenyl, 4,4'[5,5'-tetramethylene bis(1,3,4-oxadiazol-2-yl)]diphenyl, 4,4'-[5,5'-bis(1,3,4-oxadiazol-2,2'-diyl)diphenyl, 4,4'-[5,5'-m-phenylene bis(1,3,4-oxadiazol-2-yl)]diphenyl, 4,4',4''-[5,5',5''-(1,3,5-phenylene)tris(1,3,4-oxadiazol-2-yl)triphenyl and the like.

Examples of suitable 1,3,4-thiadiazol-2,5-diyl moieties are those having the structures:

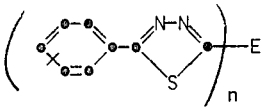

and

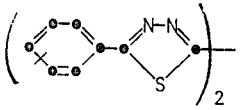

wherein E is a substituted or unsubstituted alkylene or arylene; $n$ is an integer from 1 to 6; such as 4,4'-(1,3,4-thiazol-2,5-diyl)diphenyl, 4,4'-[5,5'-tetramethylene bis(1,3,4-thiadiazol-2-yl)]diphenyl, 4,4'-[5,5'-bis(1,3,4-thiadiazol-2,2'-diyl)]diphenyl, 4,4'-[5,5'-m-phenylene bis(1,3,4-thiadiazol-2-yl)]diphenyl, 4,4',4''-[5,5',5''-(1,3,5-phenylene)tris(1,3,4-oxadiazol-2-yl)]triphenyl and the like.

Examples of suitable 1,2,4-triazol-3,5-diyl moieties are those having the structures:

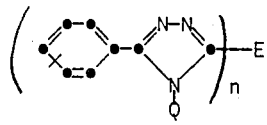

and

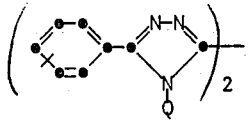

wherein E is a substituted or unsubstituted alkylene and arylene; $n$ is an integer from 1 to 6, Q is hydrogen or a substituted or unsubstituted lower alkyl group containing 1 to 12 carbon atoms; such as 4,4'-(1H-1,2,4-triazol-3,5-diyl)diphenyl, 4,4'(4H-1,2,4-triazol-3,5-diyl)diphenyl, 4,4'-[5,5'-tetramethylene bis(4H-1,2,4-triazol-3-yl)]diphenyl, 4,4'-(4-methyl-1,2,4-triazol-3,5-diyl)diphenyl, 4,4'-(1-methyl-1,2,4-triazol-3,5-diyl)diphenyl, 4,4'-[5,5'-m-phenylene bis(4-methyl-1,2,4-triazol-3-yl)]diphenyl, and the like.

Examples of suitable oxazol-diyl moieties are those having the structures:

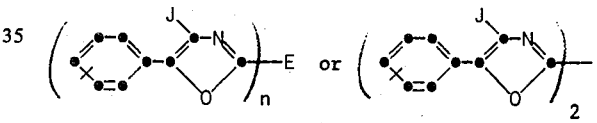

or

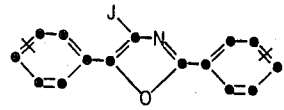

wherein E is a substituted or unsubstituted alkylene and arylene, or the same as $R_1$; J is the same as $R_1$ or a substituted or unsubstituted alkylene having 1 to 12 carbon atoms or arylene having 6 to 18 carbon atoms; $n$ is an integer from 1 to 6; such as 4,4'-(oxazol-2,5-diyl)diphenyl, 4,4'-(4-methyloxazol-2,5-diyl)diphenyl, 4,4'-(4-phenyloxazol-4,5-diyl)diphenyl, 3,4'-(4-methyloxazol-2,5-diyl)diphenyl and the like.

Examples of suitable thiazol-diyl moieties are those having the structures:

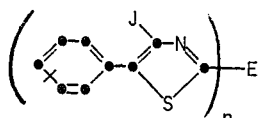

or

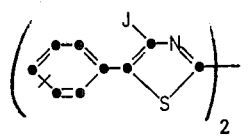

wherein E is a substituted or unsubstituted alkylene and arylene, or the same as $R_1$; J is the same as $R_1$ or a substituted or unsubstituted alkylene or arylene; n is an integer from 1 to 6; such as 4,4'-(thiazol-2,5-diyl)diphenyl, 4,4'-(4-methylthiazol-2,5-diyl)diphenyl, 4,4'-(2-methylthiazol-4,5-diyl)diphenyl, 4,4'-(thiazol-4,5-diyl)diphenyl, and the like.

Examples of suitable imidazol-diyl moieties are those having the structures:

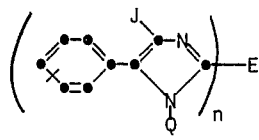

or

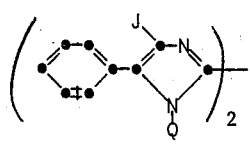

wherein E is a substituted or unsubstituted alkylene and arylene, or the same as $R_1$; J is the same as $R_1$, or a substituted or unsubstituted alkylene or arylene; n is an integer from 1 to 6; Q is hydrogen or a substituted or unsubstituted lower alkyl group having 1 to 12 carbon atoms, such as 4,4'-(imidazol-2,5-diyl)diphenyl, 4,4'-(1-methylimidazol-2,5-diyl)diphenyl, 4,4'-(2-methylimidazol-4,5-diyl)diphenyl, 4,4'-(4-methylimidazol-2,5-diyl)diphenyl, 4,4'-(1,4-dimethylimidazol-2,5-diyl)diphenyl and 4,4'-(1,2-dimethylimidazol-4,5-diyl)diphenyl and the like.

The heterocyclic compositions can be added to organic compositions which are susceptible to ultraviolet degradation. Such compositions include, for example, polymeric compositions such as polyester fiber and molding compositions, such as polyethylene terephthalate, polytetramethylene terephthalate and the like; polyolefins such as, for example, high, medium and low density polyethylene, polypropylene, polybutene and the like; polyamides such as N-methoxymethyl polyhexamethylene adipamide, nylon 66 and the like; polycarbonates; poly(vinyl chlorides) and copolymers; cellulose esters; acrylic/butadiene/styrene plastic; polyacrylics such as methyl methacrylate; polystyrene; gelatin; vinylidene chloride copolymers such as vinylidene chloride/vinyl acetate copolymers; ethylene vinyl acetate copolymers; cellulose ethers such as methyl cellulose; polyvinyl esters such as polyvinyl acetate; polyethylene oxide; polyvinyl acetals; polyformaldehydes; and polyurethanes. Such compositions also include natural and synthetic rubbers, such as polybutadiene, and unsaturated organic compositions such as oils and the like, as well as compositions containing such organic compositions.

The polychromophoric compositions, as effective ultraviolet stabilizers or screening agents, are generally used in an amount of from 0.01 to 10%, by weight, based on the weight of the organic material to which they are added. While a detectable amount of ultraviolet screening and stabilization may be obtained with amounts less than 0.01%, this amount of stabilization or screening would be of little practical utility in a commercial application. Moreover, while amounts greater than 10% by weight provide effective ultraviolet stability and screening, such concentrations are undesirable because of cost and the deleterious effect which such concentrations may have on the mechanical properties of the organic composition in which the stabilizer is incorporated. Preferably, the stabilizer is used in an amount of from about 0.1 to about 3%, by weight. For example, an amount of 2%, by weight, of the stabilizer effectively stabilizes cellulose acetate butyrate plastic compositions.

The ultraviolet stabilized organic compositions of the present invention may also contain other additives, pigments, colorants, stabilizers and the like. For example, polymeric compositions, such as polyolefins, may also contain and generally do contain other additives such as white or colored pigments or colorants, antioxidants, plasticizers, flow aids, processing aids, polymeric modifiers and the like.

These novel polychromophoric ultraviolet stabilizers may be incorporated into organic compositions by melt-blending or may be added onto the surface of an organic plastic material prior to being molded into a suitable object. These materials can also be added to coatings and the like which can be applied to the surface of a molded object.

This invention will be further illustrated by the following examples although it will be understood that these examples are included merely for purposes of illustration and are not intended to limit the scope of the invention.

EXAMPLE 1

Diphenyl-4,4'-(1,3,4-oxadiazol-2,5-diyl)dibenzoate, (I) can be prepared by the following procedure:

To a solution of hydrazine (0.01 mole) and sodium bicarbonate (15 g.) in 150 ml. of water, monoterephthaloyl chloride (0.18 mole) in 125 ml. of THF was added slowly with stirring. After stirring for an additional 30 minutes, the Product A was filtered and washed with 1 liter of water (m.p. 295°–8°, quantitative yield). A solution of A (0.056 mole) and 100 ml. of phosphorus oxychloride in 200 ml. of toluene was refluxed for 6 hours. The product B was filtered ans washed with water (m.p. 268°–270°, yield 80%). A solution of B (0.042 mole) and potassium hydroxide (0.1 mole) in 700 ml. of 60% ethanol was refluxed for 10 hours. The mixture was then acidified with 6N HCl. The product was filtered and identified as the corresponding bis acid (m.p. >300°, quantitative yield). The bis acid (0.013 mole) was refluxed with 50 ml. of thionyl chloride in 200 ml. of chlorobenzene for 10 hours. After removal of excess thionyl chloride, the product C was obtained by filtration (m.p. 208°–210°, yield 90%). To a solution of phenol (0.036 mole) and sodium hydroxide (0.025 mole) in 50 ml. of water, C (0.012 mole) in 150 ml. of chloroform was added. The mixture was refluxed for 4 hours. After cooling, Product I was obtained by filtration (m.p. 275°–280°, yield 50%).

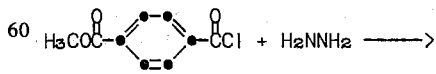

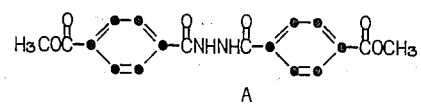

A

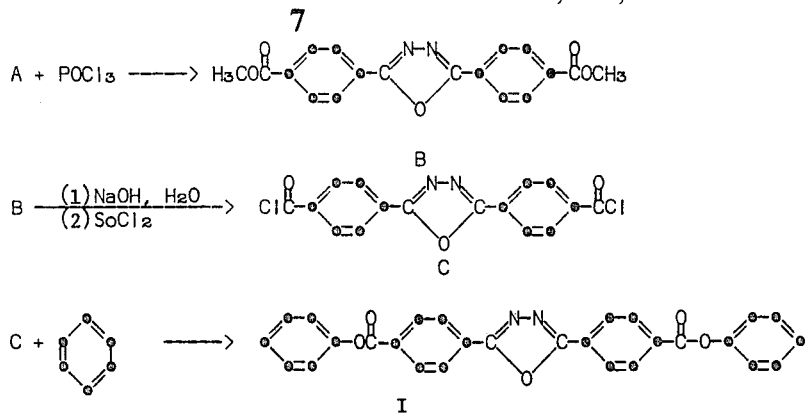

EXAMPLE 2

Bis(m-hydroxyphenyl)4,4'-(1,3,4-oxadiazol-2,5-diyl)dibenzoate, (II) can be prepared by following the same procedure as described in Example 1 (m.p. >300°, yield 50%).

EXAMPLE 3

Diphenyl-4,4'-(1,3,4-thiadiazol-2,5-diyl)dibenzoate, (III) can be prepared by the following procedure:

1,2-di(4-Carbomethoxybenzoyl)hydrazine (A), prepared as in Example 1, in pyridine was refluxed with phosphorus pentasulfide for 15 hours. The mixture was cooled and poured into 20% ethanol. After the solution was neutralized with sodium bicarbonate, the product, dimethyl-4,4'-(1,3,4-thiadiazol-2,5-diyl)dibenzoate (D), was obtained by filtration (m.p. 268°–270°, yield 60%). Then III was obtained by reacting D in a similar manner as in Example 1 (m.p. >300°, 60%).

EXAMPLE 4

Diphenyl-4,4'-(4-methyl-1,2,4-triazol-3,5-diyl)-dibenzoate (IV) can be prepared by the following procedure:

A solution of N-methyl-p-carbmethoxybenzamide in chloroform was treated with phosphorus pentachloride to give E. Then E was reacted with p-carbmethoxybenzoyl hydrazine to yield dimethyl-4,4'-(4-methyl-1,2,4-triazol-3,5-diyl)dibenzoate, (F). Then IV was obtained by reacting F in a similar manner as in Example 1.

EXAMPLE 5

Diphenyl-4,4'-(5,5'-bi-1,3,4-oxadiazol-2,2'-diyl)-dibenzoate, (V) can be prepared by the following procedure:

A mixture of oxalyl dihydrazine (0.01 mole), lithium chloride (2.0 g) and p-carbmethoxybenzoyl chloride (0.02 mole) in N-methyl pyrrolidinone (100 ml.) was stirred at room temperature overnight. The mixture was poured into 500 ml. of ice-water. The product, 1,1'-oxalylbis[2-(p-carbmethoxybenzoyl hydrazine], G, was obtained by filtration. Then V was produced by reacting G in a similar manner as in Example 1 (m.p. >300°, 50%).

EXAMPLE 6

2,5-Bis(p-benzoyloxyphenyl)-1,3,4-oxadiazole (VI) can be prepared by the following procedure:

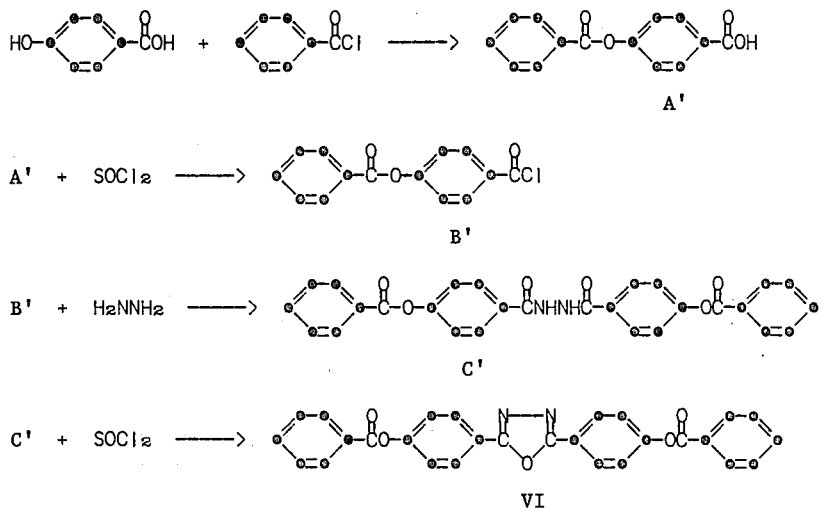

p-Hydroxybenzoic acid was refluxed with benzoyl chloride for 4 hours to give A'. A' was heated with excess thionyl chloride for 2 hours to yield B'. B' (0.1 mole) in 100 ml. N-methylpyrrolidinone was treated with .03 mol. 60% hydrazine in 50 ml. N-methylpyrrolidinone for 1 hour at 5°–10° and then stirred an additional hour at room temperature. The mixture was poured into 500 ml. ice-water and filtered to obtain C'. The mixture of C' and excess thionyl chloride was refluxed for 2 hours. After removal of thionyl chloride, the product VI, was obtained and recrystallized from toluene (m.p. 200°–3°, yield 70%).

EXAMPLE 7

Diphenyl-4,4'-(4-methyloxazol-2,5-diyl)dibenzoate (VII) can be produced by the following procedure:

α-(p-Carbomethoxybenzamido)-p-carbmethoxypropiophenone, obtained by reaction of p-carbmethoxybenzamide and α-bromo-p-carbmethoxypropiophenone, was refluxed in toluene with phosphorus oxychloride to yield 70% dimethyl-4,4'-(4-methyloxazol-2,5-diyl)dibenzoate, D'. Then VII was obtained in a similar manner as in Example 1.

EXAMPLE 8

Diphenyl-4,4'-(2-methyloxazol-4,5-diyl)dibenzoate (VIII) can be produced by the following procedure:

p,p'-Dicarbmethoxybenzoin, obtained by benzoin condensation of methyl p-formylbenzoate, was refluxed with ammonium acetate, paraldehyde in glacial arctic acid for 2 hours. The product, dimethyl-4,4'-(2-methyloxazol-4,5-diyl)dibenzoate, E', was obtained by filtration after cooling. Then VIII was obtained in a similar manner as in Example 1.

EXAMPLE 9

The ultraviolet stabilization provided by the heterocyclic stabilizer of the present invention is shown for poly(tetramethylene terephthalate) in Table 1.

A dry mixture of the stabilizer and granulated poly(tetramethylene terephthalate) was extruded into 1/16 in. diam. rods, pelletized and injection molded into 2½- × ½- × 1/16-inch flat bars; these flat bars were exposed to a 280–700 nm. mercury lamp. The test results are summarized in Table 1.

Table 1

Effectiveness of Ultraviolet Stabilizers in Poly(tetramethylene terephthalate)

| Compound (0.5%) | FWIS (Flatwise Impact Strength) | | |
|---|---|---|---|
| | Initial | 300 hr. | 500 hr. |
| None | 17 | 6 | 1 |
| I | 20 | 20 | 18 |
| II | 20 | 19 | 20 |
| III | 18 | 18 | 16 |
| IV | 19 | 17 | 15 |
| V | 20 | 20 | 20 |
| VI | 19 | 17 | 17 |
| VII | 17 | 17 | 15 |
| VIII | 18 | 16 | 14 |

These polychromophoric compositions find particular utility as ultraviolet stabilizers in organic compositions requiring ultraviolet stability. Such compositions include polymeric compositions such as, for example, polyester fiber and molding compositions, poly-α-olefins, polyamides, acrylics, cellulose esters and the like, as well as molded or shaped articles, film and coatings formed from such materials and the like. Such compositions also include natural and synthetic rubbers, as well as organic materials such as oils, fats, and unsaturated organic materials and materials having such materials contained therein such as paints, varnishes, cosmetics and the like.

The invention has been described in detail with particular reference to preferred embodiments thereof, but it will be understood that variations and modifications can be effected within the spirit and scope of the invention.

We claim:

1. An organic composition susceptible to ultraviolet degradation stabilized against such degradation with a stabilizing amount of a composition of matter comprising compounds having the formula:

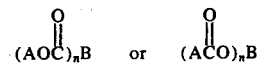

wherein A is a group having the structure:

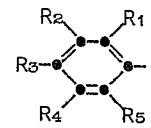

wherein $R_1$, $R_2$, $R_3$, $R_4$ and $R_5$ are hydrogen, hydroxy, chloro, bromo, fluoro, lower alkyl, substituted lower alkyl, cycloalkyl, substituted cycloalkyl, aryl, substituted aryl, lower alkylaryl, alkoxy, aryloxy, amino, substituted amino, cyano, carboalkoxy and the substituents $R_1$ and $R_2$, $R_2$ and $R_3$, $R_3$ and $R_4$, and $R_4$ and $R_5$ combined with the carbon atoms to which they are attached, are joined alkylene groups completing a carbocyclic ring, which ring can also be substituted with one or more of the substituents listed above for $R_1$, $R_2$, $R_3$, $R_4$ and $R_5$;

B is a heterocyclic group having the structures

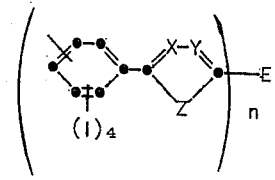

or

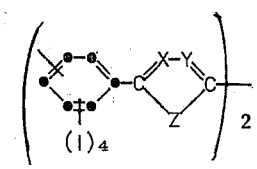

wherein

X and Y are a carbon atom, a carbon atom containing an alkyl group having 1 to 12 carbon atoms, a carbon atom containing an aryl group having 6 to 18 carbon atoms or a nitrogen atom; Z is an oxygen atom, a sulfur atom, or a nitrogen atom containing a hydrogen atom or a substituted or unsubstituted lower alkyl group having 1 to 12 carbon atoms; I is hydrogen, chloro, bromo, fluoro, lower alkyl, substituted lower alkyl, cycloalkyl, substituted cycloalkyl, aryl, substituted aryl, lower alkylaryl, aryl-substituted-aryl, alkoxy, aryloxy, substituted amino and cyano, said I is present on all positions of the benzenoid ring, except the carbon atom attached to the heterocyclic ring and the carbon atom attached to the carbonyloxy or oxycarbonyl group, E is a substituted or unsubstituted alkylene and arylene and n is an integer from 1 to 6 wherein at least one of $R_1$, $R_5$ or I ortho to the oxy of said carbonyloxy or oxycarbonyl group is hydrogen.

2. An organic composition susceptible to ultraviolet degradation stabilized against such degradation with a stabilizing amount of a composition of matter according to claim 1 having the formula

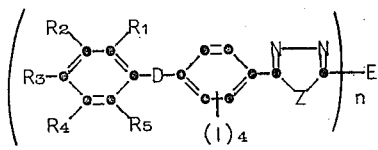

or

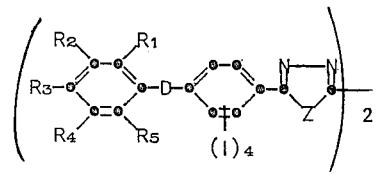

$R_1$, $R_2$, $R_3$, $R_4$ and $R_5$ are hydrogen, hydroxy, chloro, bromo, fluoro, lower alkyl, substituted lower alkyl, cycloalkyl, substituted cycloalkyl, aryl, substituted aryl, lower alkylaryl, alkoxy, aryloxy, substituted amino, cyano, carboalkoxy and the substituents $R_1$ and $R_2$, $R_2$ and $R_3$, $R_3$ and $R_4$, and $R_4$ and $R_5$ combined with the carbon atoms to which they are attached, are joined alkylene groups completing a carbocyclic ring, which ring can also be substituted with one or more of the substituents listed above the $R_1$, $R_2$, $R_3$, $R_4$ and $R_5$; D is carbonyloxy or oxycarbonyl; Z is an oxygen atom, a sulfur atom, or a nitrogen atom containing a hydrogen atom or a substituted or unsubstituted lower alkyl group having 1 to 12 carbon atoms; I is hydrogen, chloro, bromo, fluoro, lower alkyl, substituted lower alkyl, cycloalkyl, substituted cycloalkyl, aryl, substituted aryl, lower alkylaryl, aryl-substituted-aryl, alkoxy, aryloxy, substituted amino and cyano, and I is present on all positions of the benzenoid ring, except the carbon atom attached to the heterocyclic ring and the carbon atom attached to the carbonyloxy or oxycarbonyl group, E is a substituted or unsubstituted alkylene and arylene and n is an integer from 1 to 6 wherein at least one of $R_1$, $R_5$ or I ortho to the oxy of said carbonyloxy or oxycarbonyl group is hydrogen.

3. An organic composition susceptible to ultraviolet degradation stabilized against such degradation with a stabilizing amount of a composition of matter according to claim 1 having the formula

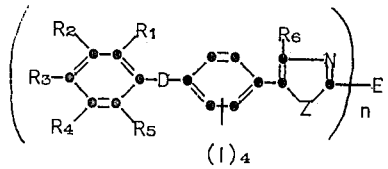

or

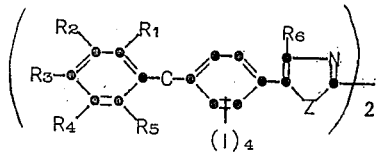

$R_1$, $R_2$, $R_3$, $R_4$, $R_5$, and $R_6$ are hydrogen, hydroxy, chloro, bromo, fluoro, lower alkyl, substituted lower alkyl, cycloalkyl, substituted cycloalkyl, aryl, substituted aryl, lower alkylaryl, alkoxy, aryloxy, amino, substituted amino, cyano, carboalkoxy, and the substituents $R_1$ and $R_2$, $R_2$ and $R_3$, $R_3$ and $R_4$, and $R_4$ and $R_5$ combined with the carbon atoms to which they are attached, are joined alkylene groups completing a carbocyclic ring, which ring can also be substituted with one or more of the substituents listed above for $R_1$, $R_2$, $R_3$, $R_4$, $R_5$ and $R_6$; D is carbonyloxy or oxycarbonyl; Z is an oxygen atom, a sulfur atom, or a nitrogen atom containing a hydrogen atom or a substituted or unsubstituted lower alkyl group having 1 to 12 carbon atoms; I is hydrogen, chloro, bromo, fluoro, lower alkyl, substituted lower alkyl, cycloalkyl, substituted cycloalkyl, aryl, substituted amino and cyano, said I is present on all positions of the benzenoid ring, except the carbon atom attached to the heterocyclic ring and the carbon atom attached to the carbonyloxy or oxycarbonyl group;
E is a substituted or unsubstituted alkylene and arylene and n is an integer from 1 to 6 wherein at least one of $R_1$, $R_5$ or I ortho to the oxy of said carbonyloxy or oxycarbonyl group is hydrogen.

4. An organic composition susceptible to ultraviolet degradation stabilized against such degradation with a stabilizing amount of a composition of matter according to claim 1 having the formula

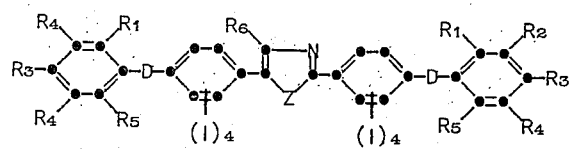

$R_1$, $R_2$, $R_3$, $R_4$, $R_5$ and $R_6$ are hydrogen, hydroxy, chloro, bromo, fluoro, lower alkyl, substituted lower alkyl, cycloalkyl, substituted cycloalkyl, aryl, substituted aryl, lower alkylaryl, alkoxy, aryloxy, amino, substituted amino, cyano, carboalkoxy, and the substituents $R_1$ and $R_2$, $R_2$ and $R_3$, $R_3$ and $R_4$, and $R_4$ and $R_5$ combined with the carbon atoms to which they are attached, are joined alkylene groups completing a carbocyclic ring, which ring can also be substituted with one or more of the substituents listed above for $R_1$, $R_2$, $R_3$, $R_4$, $R_5$ and $R_6$; D is carbonyloxy or oxycarbonyl; Z is an oxygen atom, a sulfur atom, or a nitrogen atom containing a hydrogen atom or a substituted or unsubstituted lower alkyl group having 1 to 12 carbon atoms; I is hydrogen, chloro, bromo, fluoro, lower alkyl, substituted lower alkyl, cycloalkyl, substituted cycloalkyl, aryl, substituted amino and cyano, said I is present on all positions of the benzenoid ring, except the carbon atom attached to the heterocyclic ring and the carbon atom attached to the carbonyloxy or oxycarbonyl group; E is a substituted or unsubstituted alkylene and arylene and n is an integer from 1 to 6 wherein at least one of $R_1$, $R_5$ or I ortho to the oxy of said carbonyloxy or oxycarbonyl group is hydrogen.

5. An organic composition according to claim 2 containing a stabilizing amount of a compound having the formula:

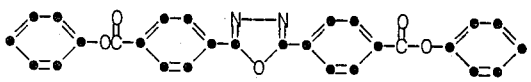

6. An organic composition according to claim 2 containing a stabilizing amount of a compound having the formula:

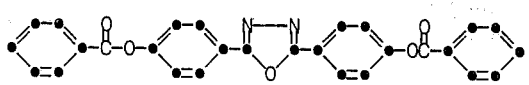

7. An organic composition according to claim 2 containing a stabilizing amount of a compound having the formula:

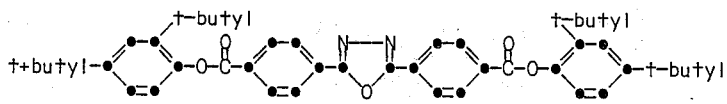

8. An organic composition according to claim 2 containing a stabilizing amount of a compound having the formula:

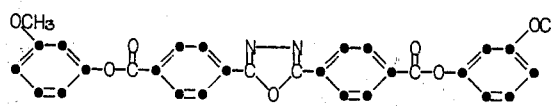

9. An organic composition according to claim 2 containing a stabilizing amount of a compound having the formula:

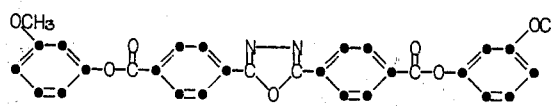

10. An organic composition according to claim 2 containing a stabilizing amount of a compound having the formula:

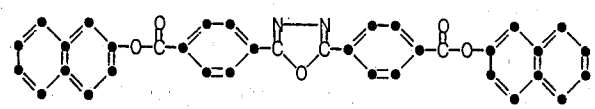

11. An organic composition according to claim 2 containing a stabilizing amount of a compound having the formula:

12. An organic composition according to claim 2 containing a stabilizing amount of a compound having the formula:

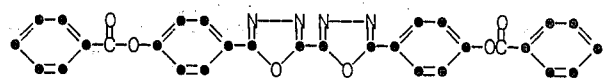

13. An organic composition according to claim 2 containing a stabilizing amount of a compound having the formula:

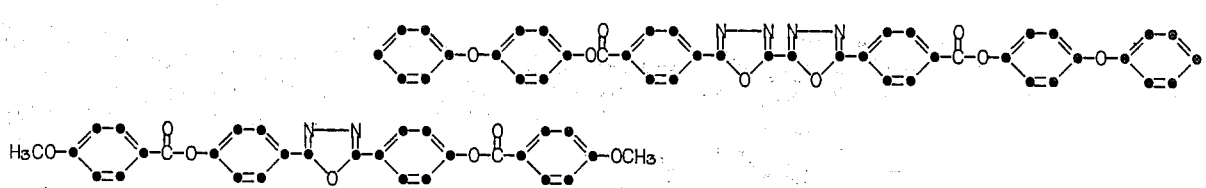

14. An organic composition according to claim 2 containing a stabilizing amount of a compound having the formula:

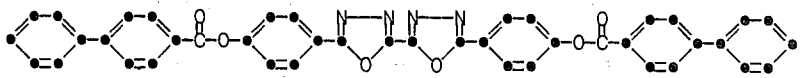

15. An organic composition according to claim 2 containing a stabilizing amount of a compound having the formula:

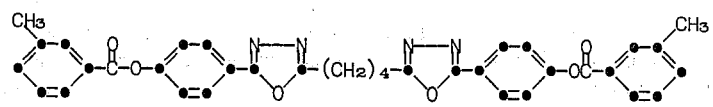

16. An organic composition according to claim 2 containing a stabilizing amount of a compound having the formula:

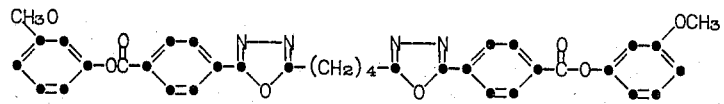

17. An organic composition according to claim 2 containing a stabilizing amount of a compound having the formula:

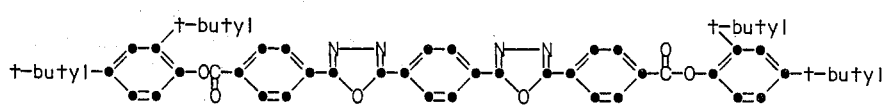

18. An organic composition according to claim 2 containing a stabilizing amount of a compound having the formula:

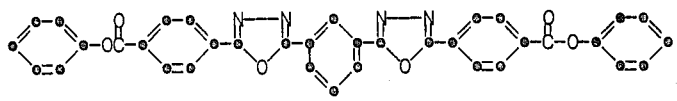

19. An organic composition according to claim 2 containing a stabilizing amount of a compound having the formula:

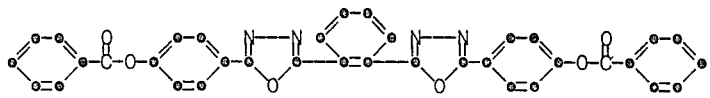

20. An organic composition according to claim 2 containing a stabilizing amount of a compound having the formula:

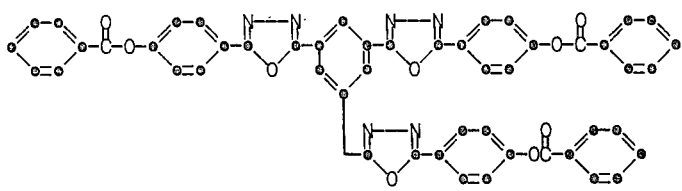

21. An organic composition according to claim 2 containing a stabilizing amount of a compound having the formula:

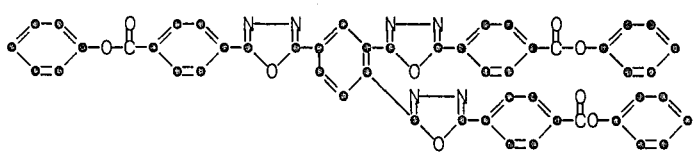

22. An organic composition according to claim 2 containing a stabilizing amount of a compound having the formula:

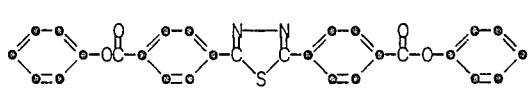

23. An organic composition according to claim 2 containing a stabilizing amount of a compound having the formula:

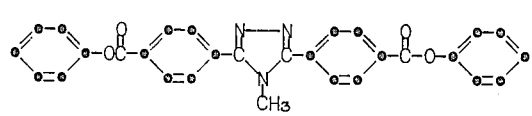

24. An organic composition according to claim 3 containing a stabilizing amount of a compound having the formula:

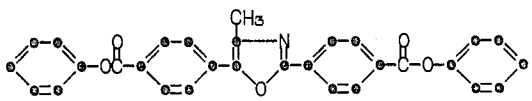

25. An organic composition according to claim 3 containing a stabilizing amount of a compound having the formula:

26. An organic composition according to claim 3 containing a stabilizing amount of a compound having the formula:

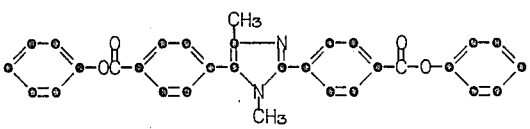

27. An organic composition according to claim 3 containing a stabilizing amount of a compound having the formula:

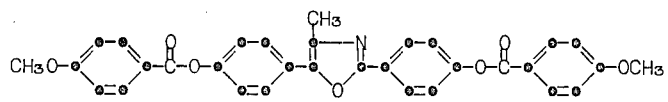

28. An organic composition according to claim 3 containing a stabilizing amount of a compound having the formula:

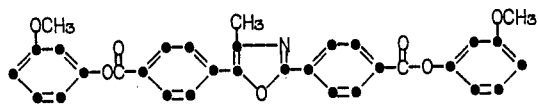
29. An organic composition according to claim 3 containing a stabilizing amount of a compound having the formula:
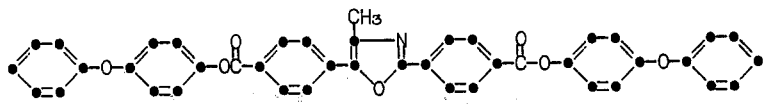
30. An organic composition according to claim 4 containing a stabilizing amount of a compound having the formula:
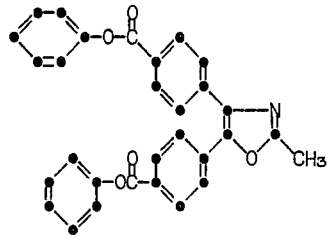
* * * * *

UNITED STATES PATENT OFFICE
CERTIFICATE OF CORRECTION

Patent No. 3,939,115     Dated February 17, 1976

Inventor(s) Richard H. S. Wang, Gether Irick, Jr.

It is certified that error appears in the above-identified patent and that said Letters Patent are hereby corrected as shown below:

Column 3, line 49, "2,2'-diyl)diphenyl," should read ---2,2'-diyl)]-diphenyl,---.

Column 3, line 52, "oxadiazol-2-yl)triphenyl" should read ---oxadiazol-2-yl)]triphenyl---.

Column 8, line 18, "(5,5'-bi-1,3,4-oxadiazol" should read ---(5,5'-bis-1,3,4-oxadiazol---.

Column 8, line 27, "V" should read ---$\nabla$---.

Signed and Sealed this

Twenty-fourth Day of August 1976

[SEAL]

Attest:

RUTH C. MASON
Attesting Officer

C. MARSHALL DANN
Commissioner of Patents and Trademarks